ROSE PLANT
Filed Sept. 13, 1973
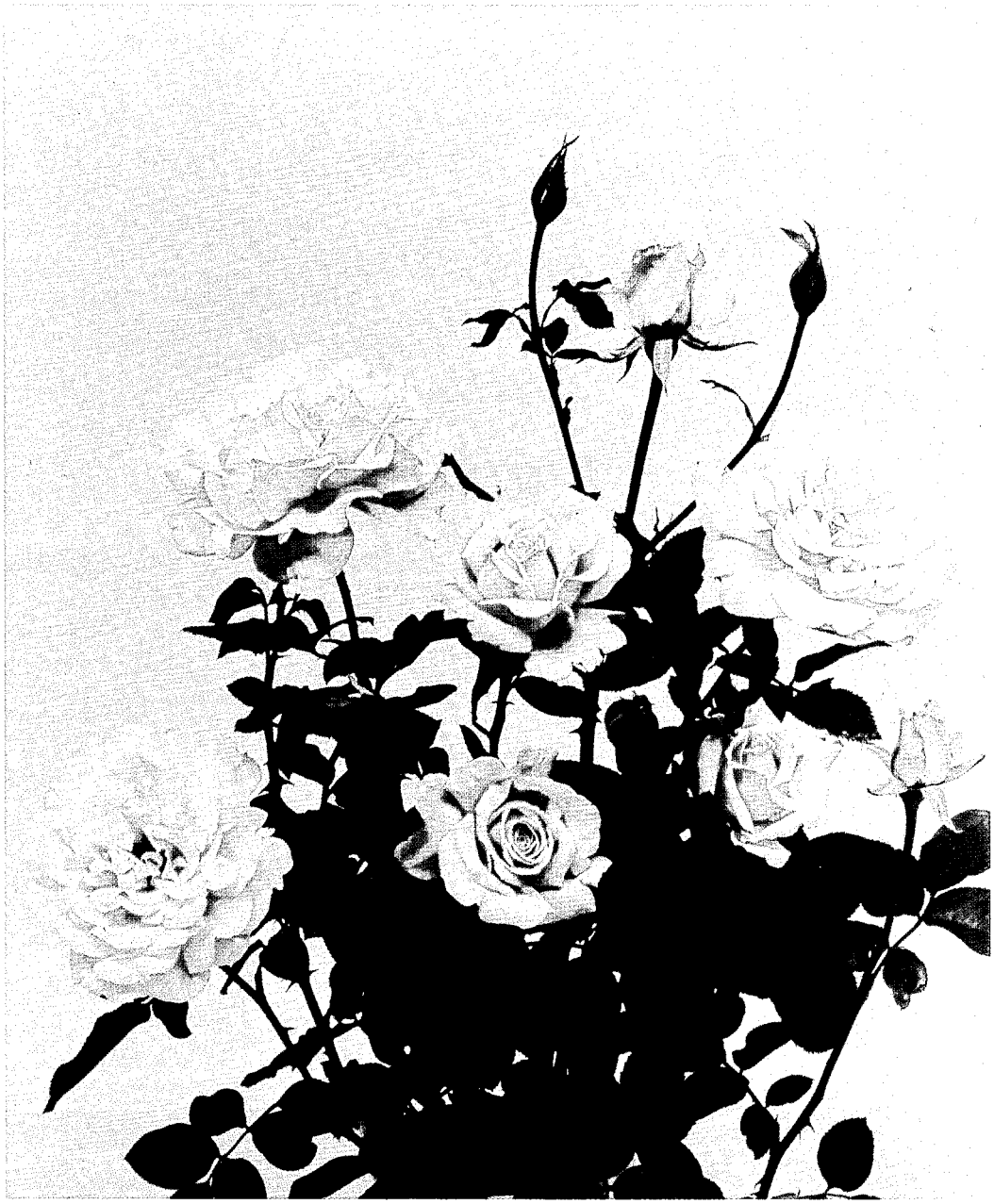

United States Patent Office

Plant Pat. 3,670

Patented Dec. 24, 1974

3,670

ROSE PLANT

Arnold W. Ellis, Upland, and Herbert C. Swim, Ontario, Calif., assignors to Armstrong Nurseries, Inc., Ontario, Calif.

Filed Sept. 13, 1973, Ser. No. 396,838

Int. Cl. A01h 5/00

U.S. Cl. Plt.—11 1 Claim

ABSTRACT OF THE DISCLOSURE

A bushy outdoor rose plant of the hybrid tea rose class being of upright-spreading habit and having abundant foliage with large dark green leaves. Notable features include: fairy large ovoid buds; strong long purplish stems, most supporting a single bloom; blooms about five inches in size; color predominantly pastel apricot; fragrance strong spicy, and fruity; and a vase life as cut flowers ranging up to six days. Petals range from forty to fifty, petaloids from five to ten, and the pistils are numerous, averaging about one hundred fifty-five per flower.

This invention relates to a new class of hybrid tea rose. The plant is a seedling of the bushy outdoor type, cultivated primarily for garden decoration. It was propagated by Arnold W. Ellis and Herbert C. Swin in Ontario, Calif., having as its seed parent "Duet" and, as its pollen parent, "Jack o' Lantern." It holds its distinguishing characteristics through succeeding propagations by budding.

The new variety bears its flowers usually singly on strong, long stems. Sometimes from two to four blooms may be carried on one stem, however. The plant blooms abundantly outdoors, and almost continuously during the growing season. It has a strong spicy and fruity fragrance.

Among the ways in which this new cultivar may be distinguished from its seed parent, Duet, may be mentioned:

The flower color of the new cultivar is pastel apricot to pastel yellowish pink, whereas, the flower color of Duet is light pink, with a dark pink or light red reverse.

The flower size of the new cultivar is from 4¾ to 5¼ inches in diameter; Duet flowers are generally notably smaller, being from 4 to 4¾ inches in diameter.

Flowers of the new cultivar comprise from about 40 to about 50 petals plus 5 to 10 petaloids, whereas flowers of Duet usually have fewer (25 to 35) petals plus 8 to 10 petaloids.

Flowers of the new cultivar have approximately 155 pistils; flowers of Duet have about 90 pistils.

Whereas the flowers of Duet are only slightly fragrant, the fragrance of this new cultivar is strong, spicy and fruity.

The new cultivar bears its blooms on long, strong stems, of substantially greater length than the medium length stems of Duet.

Features or characteristics which distinguish this new cultivar from its pollen parent, Jack o' Lantern, include:

The flower color of the new cultivar is pastel apricot to pastel yellowish pink, whereas the flower color of Jack o' Lantern is a gold and yellow blend.

Flowers of the new cultivar range in size from 4¾ to 5¼ inches in diameter, whereas the flowers of Jack o' Lantern are smaller, from 4 to 4½ inches in diameter.

The new cultivar has a significantly greater number of petals than Jack o' Lantern, namely 40 to 50 petals as compared to 20 to 30 petals.

The new cultivar has a strong fragrance, whereas Jack o' Lantern is only slightly fragrant.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values based upon the Nickerson Color Fan, put out by Munsell Color Co.

BUD

The peduncle is from average length to long, of average caliper, erect, and having numerous stipitate glands and small prickles. The color is between Strong Yellow Green, 2.5GY6/8 and Moderate Yellow Green, 2.5GY5/5, often heavily overlaid with near Dark Red, 2.5R3/7.

Before the calyx breaks, the bud is medium size, for its class, of medium length, ovoid, and has foliaceous appendages on the surface of the bud, with foliaceous parts extending beyond the tip of the bud for a distance equal to one-half or more of its length.

As the calyx breaks, the main color, where unexposed to light, is near Brilliant Yellow Green, 2.5GY8/9. Where exposed to light, the color is near Strong Red, 5R4/12. The inner surface of the sepals carries a fine, wooly tomentum.

The margins of alternate sepals are lined with a fine tomentum; margins of others with numerous foliaceous parts and numerous stipitate glands. The outer surface has some stipitate glands.

As the first petal opens, it is from average to large in size, from ovoid to urn-shaped. The color on the outside of the petal is near Brilliant Yellow Green, 2.5GY8/9, at the base; the remainder being near Moderate Orange Yellow, 7.5YR8/8, and sometimes may be irregularly overlaid with near Moderate Red, 2.5R4/10. The inside surface of the petal shows near Brilliant Yellow Green, 2.5GY9/8, at the base, the remainder being near Moderate Orange Yellow, 7.5YR8/8. The bud opens up well and is not retarded or prevented from opening by cold, hot, wet, or dry weather.

BLOOM

The size of the bloom when fully open is large, ranging from 4¾ inches to 5¼ inches. The petalage is very double, generally with from 40 to 50 petals, plus 5 to 10 petaloids arranged from regularly to irregularly. At first the bloom is cupped, full and high centered, becoming open, and high centered.

At first the petals remain somewhat cupped, with margins reflexed outward, becoming later at maturity more loosely cupped with margins reflexed outward.

Outside petals of the newly opened flower are broadly obovate, and often have 1 notch. The intermediate petals are obovate, and sometimes also have 1 notch. Inside petals are from obovate to irregular, sometimes having 1 notch.

The petals are of medium thickness, moderately leathery, with inside slightly shiny to satiny and outside shiny to satiny. The colors may be modified by being shaded and/or washed with other colors.

The description which follows is of a newly opened flower observed in the month of October. The plant had been grown outdoors, in Ontario, Calif.

The outer surface of the outside petal was generally near Brilliant Greenish Yellow, 7.5Y9/9, at the base, the remainder blending to a color between Strong Orange, 5YR6/11, and Strong Orange, 2.5YR6/12. The inner surface of the outside petal was generally near Brilliant Yellow, 2.5Y9/9, at the base, the remainder ranging between Pale Orange Yellow, 7.5YR9/4, and Light Yellowish Pink, 7.5R9/3, toward the margins.

The outer surface of both the intermediate petals and the inside petals was near Brilliant Greenish Yellow, 7.5Y9/8, at the base, the remainder being near Light Yellowish Pink, 2.5YR9/3. The inner surface of both the intermediate petals and the inside petals was near Brilliant Yellow, 2.5Y9/9, at the base, the remainder being near Pale Orange Yellow, 7.5YR9/4.

The paragraphs immediately following describe the color values observed in a bloom which had been open for three days, outdoors, in the month of October. The plant had been grown outdoors in Ontario, Calif.

The outer surface of the outside petal was near Brilliant Greenish Yellow, 7.5Y9/8, at the base, the remainder ranging between Light Orange 5YR8/7, and Moderate Yellowish Pink, 10R8/6. The inner surface of the outside petal was near Brilliant Yellow, 5Y9/9, at the base, blending to a color between Light Yellowish Pink, 2.5YR9/3, and Light Orange, 2.5YR8/6, near the margins.

The outer surface of the inside petal had a small area near the base which was near Brilliant Greenish Yellow, 7.5Y9/8, the reminder ranging between Moderate Orange Yellow, 7.5YR8/8, and Light Orange, 2.5YR8/6. The inner surface of the inside petal also had a small area near the base which was near Brilliant Greenish Yellow, 7.5Y9/8, the remainder near Light Yellowish Pink, 2.5YR9/3.

The general color effect of the newly opened flower is near Moderate Orange Yellow, 7.5YR8/8. After being three days open, the bloom gives a general color effect of between Light Yellowish Pink, 2.5YR9/3, and Light Orange, 2.5YR8/6. The petals usually drop off cleanly, and are not particularly affected by cold, hot, wet, or dry weather.

The flower on the bush in the garden persists for from 4 to 5 days in the month of October, in the locality named. Cut roses grown outdoors and kept at living-room temperatures will last from 4 to 6 days in the month of October.

REPRODUCTIVE ORGANS

Stamens: The stamens are average in number, and are arranged regularly about the pistils.

Filaments: The filaments are medium length too long, being ¼ inch to ⅜ inch long, and near Vivid Yellow, 2.5Y8/12, to near Strong Red, 5R4/12, in color. Most are with anthers.

Anthers: The anthers are medium in size, all opening approximately at once. On both the upper and under sides, they are near Vivid Yellow, 2.5Y8/12, in color.

Pollen: Pollen is from moderate to abundant, and near Brilliant Yellow, 5Y9/9, in color.

Pistils: There are many pistils, approximately 155 in number.

Styles: The styles are even to uneven, of average length to long, average caliper, and somewhat loosely bunched.

Stigma: The stigma is near Moderate Orange Yellow, 7.5YR8/8, in color.

Ovaries: Most of the ovaries are usually enclosed in the calyx, but some protrude therefrom.

Hips: Hips are of average length, and globular, with inconspicuous neck. When they are one-half to three-quarters ripe, they are near Moderate Yellow Green, 5GY5/6, in color. They are relatively smooth, with thick fleshy walls. However, relatively few hips develop on this cultivar by natural means when the plants are grown outdoors at Ontario, Calif.

Sepals: Sepals are permanent, medium-length, and somewhat recurved. The inside is near Moderate Yellow Green, 7.5GY5/7, heavily overlaid with fine tomentum. On the outside they are between Moderate Yellow Green, 5GY5/6, and Moderate Olive Green, 5GY4/3.

Seeds: Seeds are few in number, from 1 to 4, and are from medium size to large.

FOLIAGE

The *compound leaves* usually comprise three to seven leaflets, present in normal quantity. They are from medium size to large, heavy and glossy. The *leaflets* are ovate, with apex acute, base obtuse, and margin simply to irregularly serrate.

The *mature foliage* displays upon its upper surface a color which is between Moderate Olive Green, 5GY4/3, and Grayish Olive Green, 5GY3/2. The under surface is grayer than but somewhat between Strong Yellow Green, 7.5GY7/9, and Strong Yellow Green, 7.5GY6/8, lightly overlaid with near Deep Purplish Red, 7.5RP3/9.

The *young foliage* on its upper surface has a general color effect between Dark Red, 5R3/7, and Dark Red, 2.5R3/7, with some light to dark olive green showing through the red. The under surface is generally between Dark Red, 2.5R3/7, and Deep Purplish Red, 7.5RP3/9.

The *rachis* is of average size, grooved, with many stipitate glands on the edges. The under side is sparsely prickly and with few stipitate glands.

*Stipules* are medium-length, medium-width, and with medium-length points turning out at an angle of about 45°, often recurved toward the stem.

The plant displays an average resistance to mildew, when compared to like varieties grown under comparable conditions at Ontario, Calif.

GROWTH

The plant is of bushy, upright-spreading habit, moderately branched. Its growth is vigorous, and the canes are of medium to heavy caliper.

The *main stems* are between Moderate Olive, 5Y4/3, and Light Olive, 10Y5/5, in color. They bear several medium-length to long large prickles which are almost straight to hooked slightly downward, with medium-length, moderately broad bases. These large prickles are between gray and Strong Brown, 5YR4/5, in color. There are few small prickles, and these are the same color as the large prickles. There are no hairs.

The coloration of the *branches* is near Moderate Yellow Green, 5GY5/6, lightly to very heavily overlaid with near Deep Purplish Red, 7.5RP3/9. These have from few to several large prickles, which are medium-length to long, hooked slightly downward, with medium-length, moderately narrow bases. These large prickles are between Moderate Brown, 7.5YR4/5, and Dark Red, 5R3/7, in color. There are few small prickles, and the color of these is the same as the large prickles. There are no hairs.

*New shoots* have a color between Strong Yellow Green, 5GY7/10, and Strong Yellow Green, 5GY6/8, heavily overlaid, except where well shaded, with between Dark Red, 2.5R3/7, and Deep Purplish Red, 7.5RP3/9. These shoots have several medium-length to long large prickles whcih are hooked slightly downward, with medium-length moderately narrow bases. These have a color which is near Strong Yellow Green, 2.5GY7/10, at the point, the remainder being near Dark Red, 5R3/7. There are from none to few small prickles, and these are the same color as the large prickles. There are no hairs.

We claim:

1. A rose plant of the hybrid tea rose class, substantially as herein illustrated and described, being of bushy, upright-spreading habit with abundant large dark green leaves, said plant being particularly notable in its large ovoid buds, usually singly supported on strong long purplish stems; in the large size, about five inches across, of the blooms, and by the pastel apricot color of the 40 or 50 petals and 5 to 10 petaloids; the blooms further being notable for their strong spicy or fruity fragrance, and their vase life as cut flowers, being from four to six days.

No references cited.

ROBERT E. BAGWILL, Primary Examiner